(12) United States Patent
Matsushita et al.

(10) Patent No.: US 6,999,166 B2
(45) Date of Patent: Feb. 14, 2006

(54) COMPONENT, APPARATUS, AND METHOD FOR ANALYZING MOLECULES

(75) Inventors: Tomohiko Matsushita, Osaka (JP); Takeo Nishikawa, Osaka (JP); Shigeru Aoyama, Kyoto (JP)

(73) Assignee: Omron Corporation, Kyoto (JP)

( * ) Notice: Subject to any disclaimer, the term of this patent is extended or adjusted under 35 U.S.C. 154(b) by 244 days.

(21) Appl. No.: 10/614,723

(22) Filed: Jul. 7, 2003

(65) Prior Publication Data
US 2004/0080746 A1   Apr. 29, 2004

(30) Foreign Application Priority Data
Jul. 8, 2002   (JP) ............... 2002-199088

(51) Int. Cl.
*G01N 21/01*   (2006.01)
*G01N 21/64*   (2006.01)
(52) U.S. Cl. ................................ 356/317; 356/244
(58) Field of Classification Search ........... 356/244, 356/246, 317–318, 417; 250/458.1–461.2; 422/99
See application file for complete search history.

(56) References Cited
U.S. PATENT DOCUMENTS
5,736,410 A * 4/1998 Zarling et al. ........... 250/458.1
6,473,239 B1   10/2002 Völcker et al.
6,552,794 B2 * 4/2003 Garini .................... 356/445
6,686,582 B1 * 2/2004 Volcker et al. ......... 250/461.2
2002/0154408 A1 * 10/2002 Minoura et al. ............ 359/529

FOREIGN PATENT DOCUMENTS
JP    3-188408    8/1991
JP    2001-083296   7/2001

OTHER PUBLICATIONS
Patent Abstracts of Japan, Publication No.: 2001-183296, Publication Date: Jul. 6, 2001, 2 page.
Patent Abstracts of Japan, Publication No.: 02-188408, Publication Date: Aug. 16, 1991, 2 pages.

* cited by examiner

*Primary Examiner*—Gregory J. Toatley, Jr.
*Assistant Examiner*—Kara Geisel
(74) *Attorney, Agent, or Firm*—Osha Liang LLP (57) ABSTRACT

Components, apparatus, and method for detecting emission signals from target molecules include a substrate having a plurality of pixel locations on a surface, each location including at least one target molecule; a reflecting plate disposed opposite a side of the substrate having the pixel location; and a lens array disposed between the substrate and the reflecting plate, including the first lens array on the substrate side, a medium layer, and the second lens array on the reflecting plate side. Each lens of the second lens array has its focus on each lens of the first lens array, and the first lens array and the second lens array focus into an image of each of the at least one target molecule on the reflecting plate.

10 Claims, 6 Drawing Sheets

PRIOR ART

COMPONENT, APPARATUS, AND METHOD FOR ANALYZING MOLECULES

BACKGROUND OF INVENTION

1. Field of the Invention

This invention relates to a component, an apparatus, and a method for analyzing molecules, and more particularly to a component, an apparatus, and a method for detecting emission signals from target molecules.

2. Description of the Prior Art

A method for detecting chemical interactions between two materials has been conventionally used representatively to determine whether DNA hybridization has occurred. For example, a plurality of probe molecules are provided on a substrate for possible reactions with sample molecules carrying binding partners. The sample molecules are fluorescently or electrochemically labeled. It is possible to estimate presence or degree of interactions between each probe molecule and each sample molecule by detecting emission signals from labeled molecules. The substrate including those target molecules may be referred to as a chip or an array.

Figure 6:
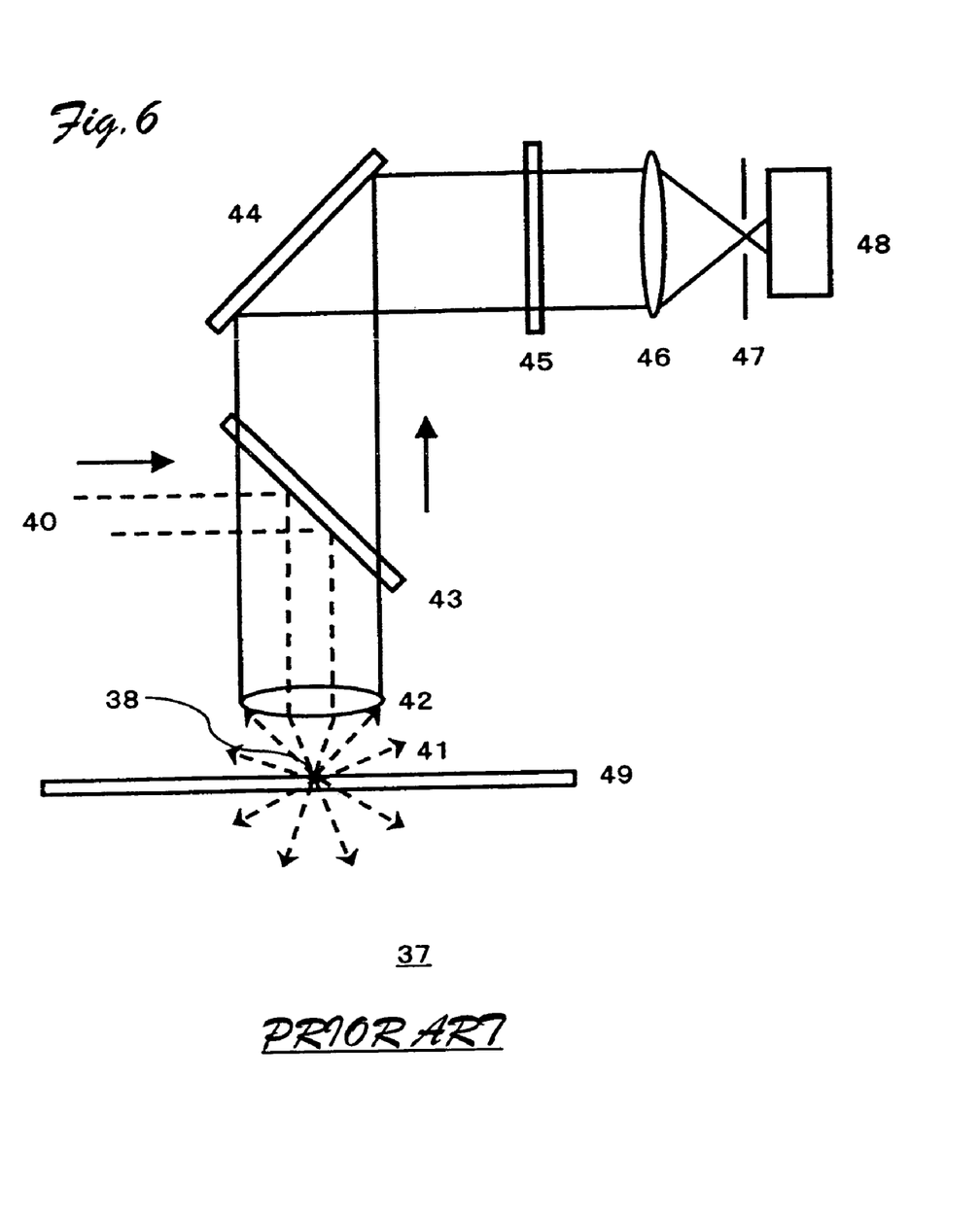
FIG. 6 is a simplified sectional view of a conventional light detecting apparatus.

In FIG. 6, there is shown a light detecting apparatus 37 employed in such a conventional method. The apparatus 37 includes a substrate 49 on which a plurality of samples 38 are arranged, an object lens 42, a beam splitter 43, a mirror 44, an emission filter 45, a light receiving lens 46, a focus pinhole 47, and a light receiver 48. Excitation beams 40 projected by an excitation beam generator (not shown) are reflected by the beam splitter 43 and directed to a sample 38. The sample 38 excited by the beam emits emission signals 41. Emission signals 41 are received by the object lens 42 which is disposed over the sample 38, passed through the beam splitter 43, lead to the emission filter 45 by way of the mirror 44, gathered by the light receiving lens 46, eliminated of noise signals by the focus pinhole 47, and detected by the light receiver 48.

When electrochemically labeled materials are included in the sample 38, the excitation beam 40 is not applied, but emission signals 41 are emitted from the sample 38 and received by the light receiver 48 in the same way.

The emission signal 41 emitted from the sample 38 is weak. Furthermore, according to the conventional apparatus 37, the amount of the emission signals that can be detected depends on a numerical aperture (NA) of the object lens 42, which means that only emission signals that emitted within the area of the object lens 42 can be detected. Therefore, most of the amount of the emission signals 41 is not detected, and the efficiency of detecting signals is not desirable.

SUMMARY OF THE INVENTION

According to one embodiment of this invention, there is provided a component for analyzing molecules which includes a transparent substrate having a plurality of pixel locations on a first surface thereof, each location including at least one target molecule, a reflecting plate arranged to face an opposite side of the first surface of the substrate, and a. micro lens array interposed between the substrate and the reflecting plate, which includes a first lens array next to the substrate, a second lens array next to the reflecting plate, and a medium layer interposed between the first and second lens arrays, wherein each lens of the second lens array has its focus on each opposing lens of the first lens array, and the first lens array and the second lens array focus into an image of each of the target molecules on the reflecting plate.

According to one embodiment of this invention, there is provided a component for analyzing molecules that includes a transparent substrate having a plurality of pixel locations on a first surface thereof, each location including at least one target molecule, and a corner cube array arranged to face an opposite side of the first surface of the substrate, and designed to reflect an incoming ray of light exactly in the same direction as It entered the corner cube array.

According to one embodiment of this invention, there is provided a method for analyzing molecules that includes steps of applying an excitation beam generated by an excitation beam generator to at least one target molecule arranged on a transparent substrate, controlling optical paths of emission signals emitted from the excited at least one target molecule by a micro lens array or a corner cube array, detecting the emission signals, and analyzing one or more values of detected emission signals.

BRIEF DESCRIPTION OF DRAWINGS

The above and other features of this invention will be more clearly understood from the following detailed description provided in conjunction with accompanying drawings, of which.

DETAILED DESCRIPTION OF THE INVENTION

Figure 1:
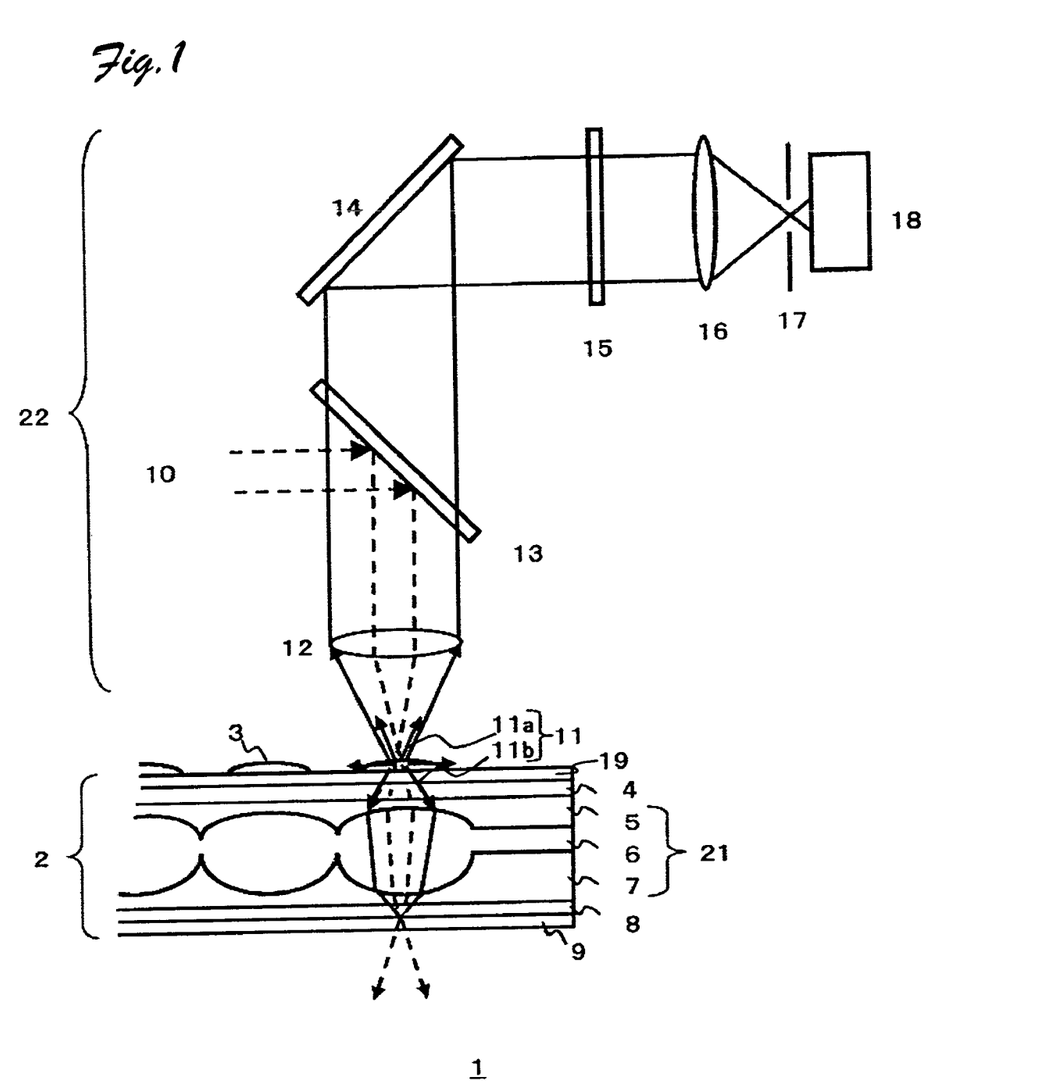
FIG. 1 is a simplified, sectional view of a light detecting apparatus according to a first embodiment of this invention.

FIG. 1 shows a simplified sectional view of a light detecting apparatus according to a first embodiment of this invention.

A light detecting apparatus 1 includes a light detecting system 22 and a component 2 disposed under the light detecting system 22. The light detecting system 22 includes an object lens 12, a beam splitter 13, a mirror 14, an emission filter 15, a light receiving lens 16, a focus pinhole 17, and a light receiver 18.

The component 2 includes a main substrate 19 having a plurality of samples 3 arranged on a first surface thereof, a first substrate 4, a micro lens array 21, a second substrate 8, and a reflecting plate, arranged in the order shown in FIG. 1.

The micro lens array 21 includes a first lens array 5 next to the main substrate 19, a second lens array 7 next to the reflecting plate 9, and a. medium layer 6 interposed between the first array 5 and the second lens array 7, wherein each lens of the second lens array 7 has its focus on each opposing lens of the first lens array 5, and the first lens array 5 and the second lens array 7 focus into an image of each of the samples 3 on the reflecting plate 9. The samples 3 may be disposed directly on the first substrate 4 or the first lens array 5 without using the main substrate 19.

With the use of the component like this, emission signals emitted from the sample in the direction of the micro lens array can be controlled by the functions of the micro lens array and the reflecting plate so as to return to the point where the signal was emitted.

The medium layer 6 can be made of any material that is light permeable such as light permeable resin. The medium layer 6 integrates the first lens array 5 and the second lens array 7. Integrating the first lens array 5 and the second lens array 7 makes handling easier and keeps both lens arrays in position even if time passes.

The medium layer 6 also can be made of gas. In such a case, the first lens array 5 and the second lens array 7 may be integrated at the ends of the micro lens array 21 where lenses are not formed. In such a case, the difference of the reflective indexes between the both lens arrays and the medium layer is great, and the NA of the lens is large. Therefore, the amount of emission signals that can be captured by the lens increases and the light detecting efficiency is improved.

The main substrate 19, the first substrate 4, the micro lens array 21, and the second substrate 8 are made of transparent material that permeates emission signals.

An operation of the light detecting apparatus 1 will be described hereinafter. Excitation beams 10 projected by an excitation beam generator (not shown) are reflected by the beam splitter 13 and directed to samples 3. A fluorescently labeled sample excited by the beam emits emission signals 11. Emission signals 11*a* emitted in the direction of an object lens 12 are received by the object lens 12 within the limits of the NA of the lens. On the other hand, emission signals 11*b* emitted in the direction of the micro lens array 21 are received by the first lens array 5, refracted at one boundary between the first lens array 5 and the medium layer 6 and another boundary between the medium layer 6 and the second lens array 7, and reflected by the reflecting plate 9.

Total emission signals 11 captured by the object lens 12 are passed through the beam splitter 13, lead to the emission filter 15 by way of the mirror 14, gathered by the light receiving lens 16, eliminated of noise signals by the focus pinhole 17, and detected by the light receiver 18.

An excitation beam 10 that passes through the sample 3 is also received and refracted by the micro lens array 21 and reaches the reflecting plate 9. If the excitation beam 10 is reflected by the reflecting plate 9 and captured by the object lens 12, it would be a "noise." However, if a reflecting plate that can permeate or absorb light having a predetermined wavelength, such as a band-pass filter, is employed, the excitation beam 10 is not reflected by the reflecting plate 9. With the use of a specific type of reflecting plate 9 like this, only the emission signals emitted, from the sample can be reflected by the reflecting plate 9, and detection of the signals is made with high efficiency.

The relationship between the refractive index and the configuration of the first lens array 5, the second lens array 7, and the medium layer 6 will be described hereinafter. Assuming the refractive index of the first lens array 5 is n1, the refractive index of the medium layer 6 is n2, and the refractive index of the second lens array 7 is n3, in a case in which each of the lens arrays is convexly curved against the outer surface of the component as shown in FIG. 1, the relationships of the refractive indexes are n1<n2 and n3<n2.

The medium layer 6 can be made of gas or resin. If some resin is used as a medium layer 6, the coefficient of thermal expansion of that resin may be almost the same as those of the first lens array and the second lens array. This improves tolerance to the surroundings and decreases deterioration of micro lens array as time passes.

In a case in which each of the lens arrays is concavely curved against the outer surface of the component (not shown in any drawings), the relationships of the refractive indexes are n1>n2 and n3>n2. In a case in which the first lens array 5 is convexly curved and the second lens array 7 is concavely curved against the outer surface of the component (not shown in any drawings), the relationships of the refractive indexes are n1<n2<n3, and vice versa.

FIG. 1 is a schematic view, and is drawn irrespective of the difference between the refractive index of each component.

Figure 2A:
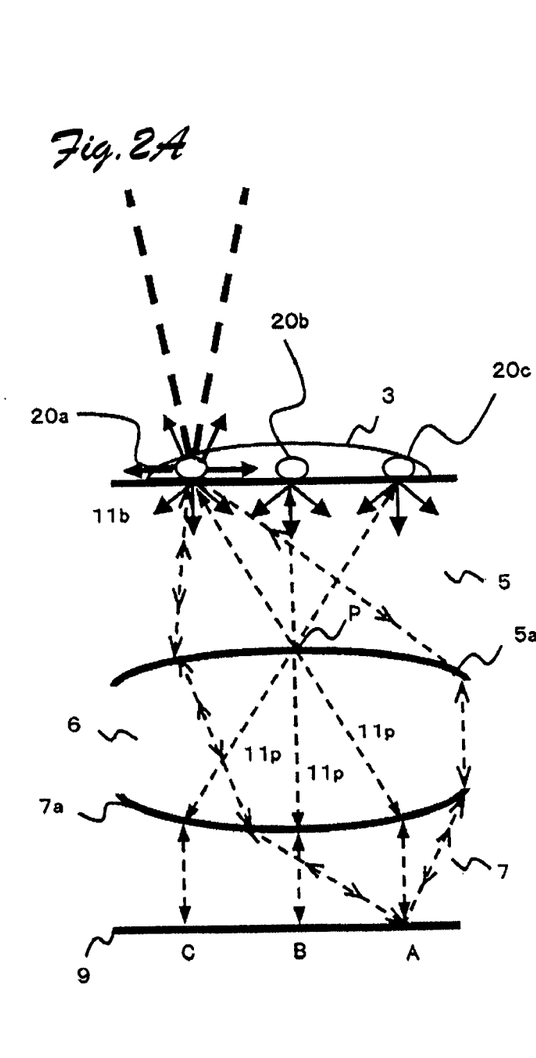
FIG. 2A is a simplified partial sectional view showing a configuration of a component employed in the apparatus of FIG. 1.
Figure 2B:
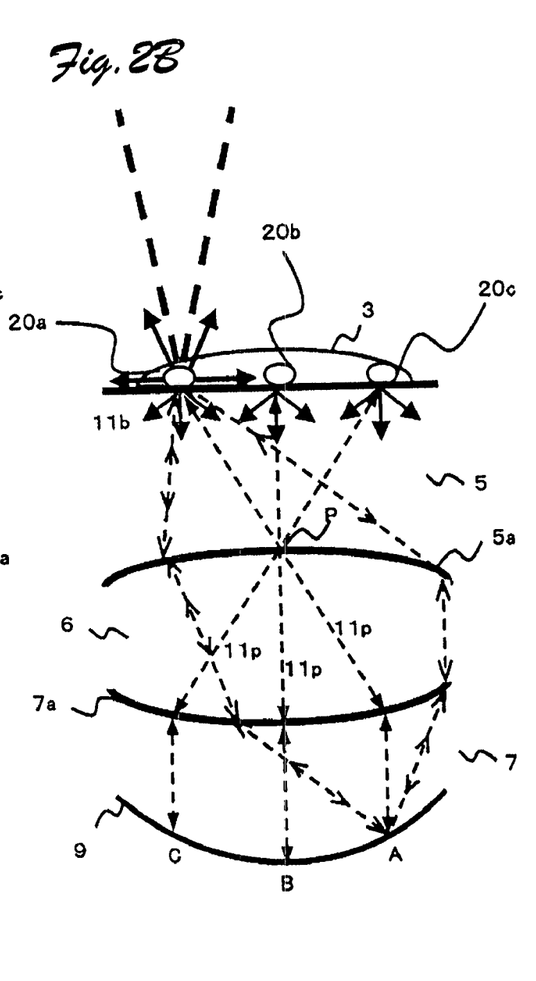
FIG. 2B is a simplified partial sectional view showing a configuration of another component employed in the apparatus of FIG. 1.

In FIGS. 2A and 2B, there are shown simplified partial sectional views representing a configuration of a component employed in the apparatus of FIG. 1. These figures show the optical path of emission signals 11*b*) emitted from the sample 13 in the direction of the micro lens array. In FIGS. 2A and 2B, the first substrate 4, the second substrate 8 etc. are not drawn for convenience of explanation.

Each lens 5*a* of the first lens array 5 and each lens 7*a* of the second lens array 7 are arranged so that each lens 7*a* has its focus on the surface (i.e. the boundary between the first lens array 5 and the medium layer 6) of each opposing lens 5*a*. In one embodiment, each lens 7*a* has its focus at the middle of the surface of each opposing lens 5*a*. Therefore, among emission signals 11*b* emitted from the fluorescent molecules 20*a*, 20*b*, and 20*c*, emission signals 11*p* that pass a point P (i.e., a focus of the lens 7*a*) on the surface of the lens 5*a* are refracted by the micro lens array to be parallel with each other, and reach the reflecting plate 9 at points A, B, and C. Each emission signal 11*p* reflected by the reflecting plate 9 travels back to the positions of the fluorescent molecules 20*a*, 20*b*, and 20*c* by way of the point P, and is emitted from those positions in the direction of the object lens.

The configurations and the refractive indexes of the lens 5*a*, the lens 7*a*, and the medium layer 7 are determined so that an image of fluorescent molecules 20 is formed on the reflecting plate 9. Therefore, among emission signals 11*b* emitted from the fluorescent molecules 20*a*, 20*b*, and 20*c*, emission signals that do not pass a point P are also refracted by the first lens array 5 and the second lens array 7, and reach the reflecting plate 9 at points A, B, and C.

In a case in which a point P (i.e., a focus of the lens 7*a*) is provided at the middle of the surface of the lens 5*a*, emission signals 11*b* received by the first lens array 5 within the limits of the NA reach the reflecting plate 9 at points A, B, and C with substantially symmetrical incident angles. Therefore, almost all of the emission signals 11*b* reflected by the reflecting plate 9 return to the positions of the fluorescent molecules 20*a*, 20*b*, and 20*c*, and are emitted from those positions in the direction of the object lens.

The point P is not necessarily at the middle of the surface of the lens 5*a*, and emission signals 11*b* return to the positions of the fluorescent molecules 20*a*, 20*b*, and 20*c*, by following almost the same paths as long as the point P is provided on the surface of the lens 5*a*.

As described above, emission signals 11*b* emitted from the fluorescent molecules 20*a*, 20*b*, and 20*c* in the direction of the micro lens array 21 are returned to the positions of the fluorescent molecules 20*a*, 20*b*, and 20*c* by the functions of the micro lens array 21 and the reflecting plate 9, emitted from those positions as if they were originally emitted from the fluorescent molecules 20a, 20b, and 20c in the direction of the object lens 12, and detected by the light detecting system 22.

With the use of the component as described above, almost twice as many emission signals from each fluorescent molecule 20 as before are captured by the light receiver 18.

The reflecting plate 9 may have a flat surface as shown, in FIG. 2A or a curved, surface as shown in FIG. 2B. An aberration of the micro lens array fails to focus into an image of each fluorescent molecule 20a, 20b, and 20c on the same plane. In a case in which the reflecting plate 9 has a curved surface, however, the aberration of the micro lens array 21 is counteracted. Therefore, reflected signals are precisely returned to the positions of the fluorescent molecules 20a, 20b, and 20c. Further, the curved surface of the reflecting plate 9 makes reflecting angles at points A, B, and C on the reflecting plate 9 smaller, so that reflected signals are efficiently returned to the original positions even if the reflected signals are emitted from a fluorescent molecule placed near the side of the sample 3.

Figure 3:
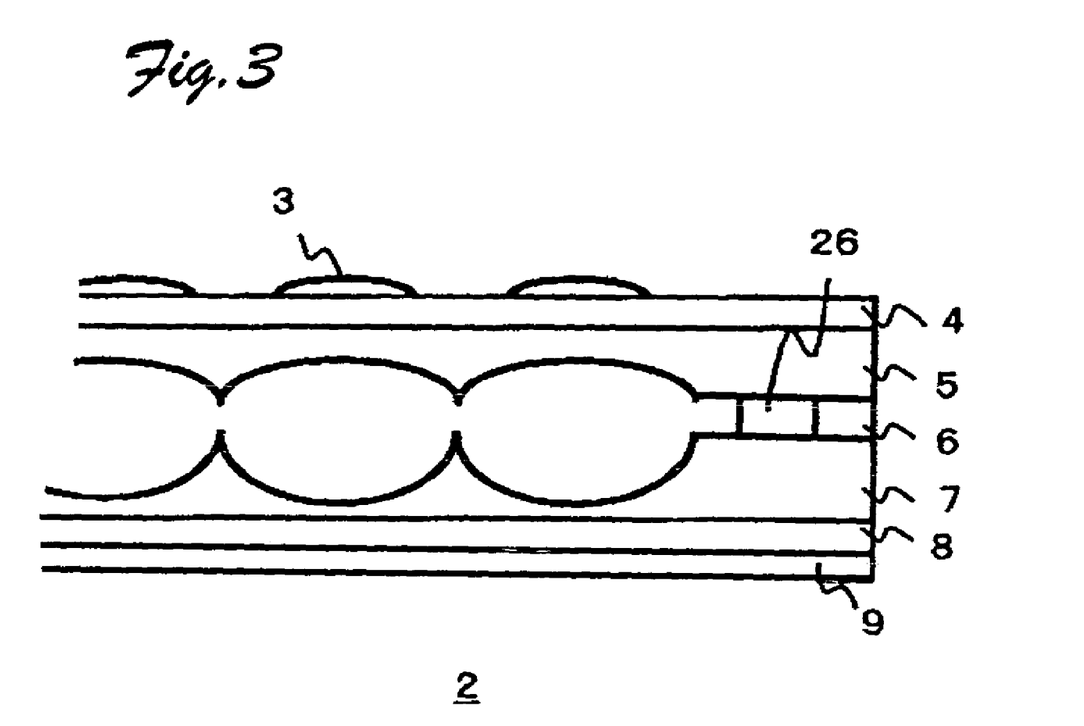
FIG. 3 is a simplified partial sectional view of a component employed in the apparatus of FIG. 1.

The micro lens array 21 may also be composed of more than three lens arrays. With the use of more than three lens arrays, an aberration of the micro lens array can be counteracted, and optical characteristics of the micro lens array improve. FIG. 3 shows a simplified partial sectional view of a component employed in the apparatus of FIG. 1. As shown in FIG. 3, a spacer 26 may be used between the first lens array 5 and the second lens array 7 at the ends of the lens arrays where lenses are not formed. The spacer 26 makes it easier to adjust the disposition of the lens arrays.

Figure 4:
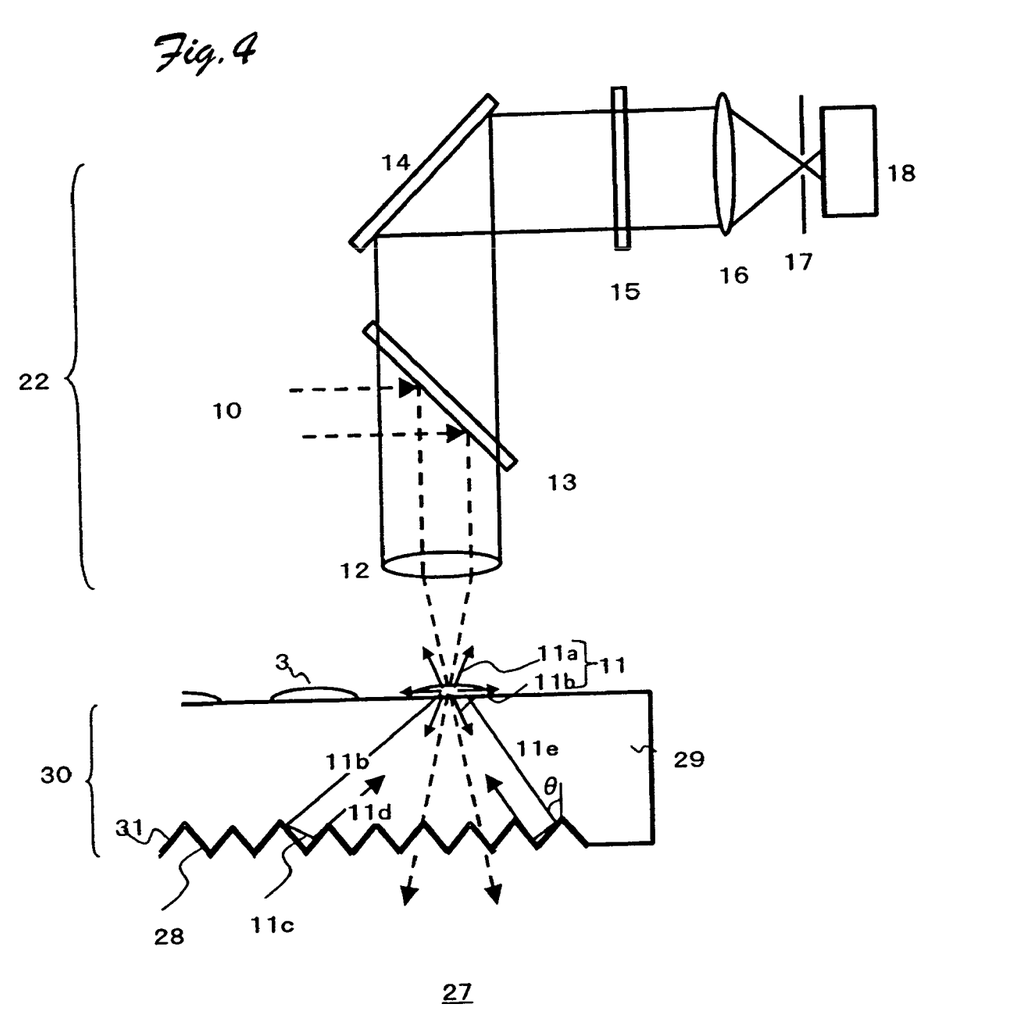
FIG. 4 is a simplified sectional view of a light detecting apparatus according to a second embodiment of this invention.

FIG. 4 shows a simplified sectional view of a light detecting apparatus 27 according to a second embodiment of this invention. The light detecting apparatus 27 includes a light detecting system 22 and a component 30. The light detecting system 22 is the same as one described in FIG. 1, and is not explained again here.

The component 30 includes a transparent substrate 29 having a plurality of samples 3 on a first surface thereof and a corner cube array 31 arranged to face an opposite side of the first surface of the substrate and designed to reflect an emission signal 11 emitted from a sample 3 in the same direction as it entered the corner cube array 31. A prism that reflects an incoming ray of light exactly in the same direction as it entered the prism is referred to as a corner cube array. A corner cube array may be provided with a band-pass filter 28.

An operation of the light detecting apparatus 27 will be described below. Excitation beams 10 projected by an excitation beam generator (not shown) are reflected by the beam splitter 13 and directed to samples 3. A fluorescently labeled sample 3 excited by the beam emits emission signals 11. Emission signals 11a emitted in the direction of the object lens 12 are received by the object lens 12 within the limits of the NA. Also, emission signals 11b emitted in the direction of the corner cube array 31 are reflected on the several reflecting surfaces of the corner cube array 31, returned to the position of the sample 3, and received by the object lens 12. The emission signals 11a and 11b received by the object lens 12 are passed through the beam splitter 13, lead to the emission filter 15 by way of the mirror 14, gathered by the light receiving lens 16, eliminated of noise signal by the focus pinhole 17, and detected by the light receiver 18.

An excitation beam 10 that passed through the sample also reaches the corner cube array 31. If the excitation beam 10 is reflected by the corner cube array 31 and captured by the object lens 12, it would be a "noise." However, if reflecting plate that can permeate or adsorb light having a predetermined wavelength, such as a band-pass filter 28, is provided with the corner cube array 31, the excitation beam 10 is not reflected by the corner cube array 31. Therefore, only emission signals emitted from the sample can be reflected by the corner cube array 31, and light detection is made with high efficiency.

As described above, emission signals 11b emitted from a fluorescent molecule in the direction of the corner cube array 31 are returned to the position of the fluorescent molecule by the function of the corner cube array 31, emitted from that position as if they were originally emitted from the fluorescent molecule in the direction of the object lens 12, and detected by the light receiver 18.

With the use of the component as described above, almost twice as many emission signals from each fluorescent molecule as before are captured by the light receiver 18.

In one embodiment, the corner cube array 31 is designed such that the width of each prism of the corner cube array 31 is narrower than the width of each sample 3, whereby emission signals emitted from the sample 3 in the direction of the corner cube array 31 are returned to the position of the sample 3 efficiently.

As shown in FIG. 4, the incident angle $\theta$ with which the emission signal 11e emitted from the sample 3 into the reflecting surface of the corner cube array 31 is maximally $\sin^{-1}(n_b/n_a)$, that is critical angle where $n_a$ is the refractive index of the substrate 29 and $n_b$ is the refractive index of the sample 3. Assuming the area where corner cubes are formed is area A, the area vertically projected on the reflecting surface of the corner cube array 31 where the samples 3 are arranged is area B, the distance from the sample 3 to the reflecting surface of the corner cube array 31 is d, and the incident angle with which the emission signal 11e emitted from the sample 3 into the reflecting surface of the corner cube array 31 is $\theta$, in one embodiment, the extremity of area A is apart from the extremity of area B by at least d·tan $\theta$, so that emission signals emitted from a sample disposed near the end of the substrate can be successfully reflected. When $n_a$ is 1.5, for example, $\theta$ would be maximally 42°. Therefore, the extremity of the area A should be apart from one of the area B by at least d.

As described above, with the use of the light detecting apparatus according to an embodiment of the invention, emission signals emitted in the opposite direction of the object lens are detected as well as emission signals emitted in the direction of the object lens. Therefore, weak signals can be detected efficiently.

The embodiments described above are provided for analyzing fluorescently labeled molecules, but it is clear that electrochemically labeled molecules can be analyzed with the same effects according to embodiments of the component of the invention. In a case in which electrochemically labeled materials are used, the application of the excitation beam 10 is not necessary, and use of a band-pass filter is not necessary.

Figure 5:
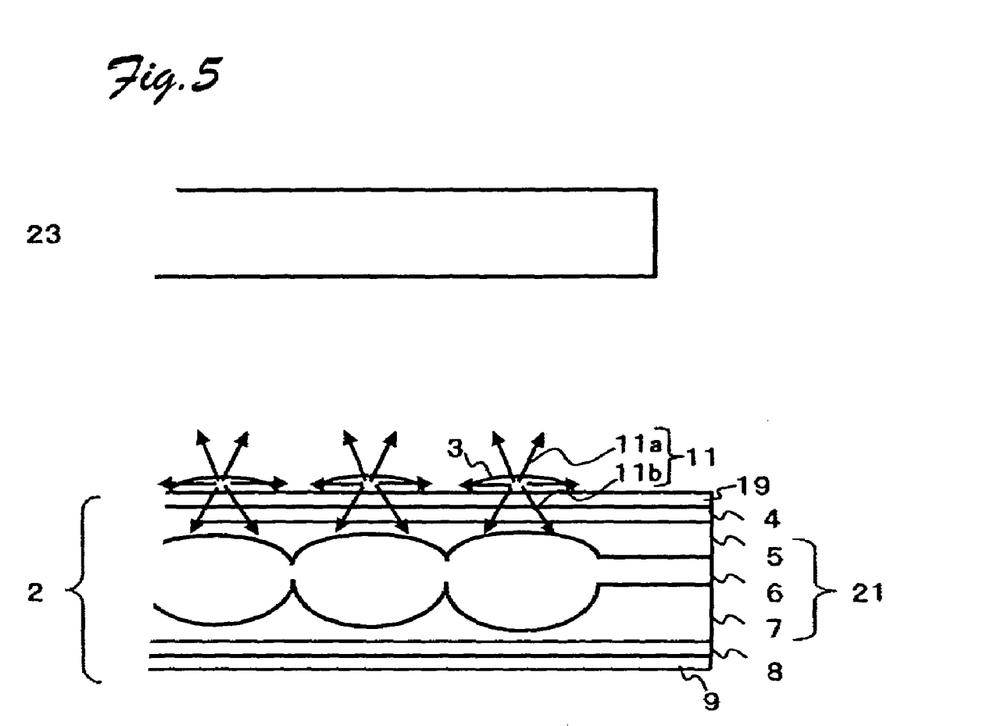
FIG. 5 is a simplified partial sectional view of a light detecting apparatus according to a third embodiment of this invention.

In the embodiments described above, the light detecting system 22 is explained when a photo-multiplier is used as a light receiver 18. As shown in FIG. 5, however, a CCD camera 23 can be substituted for the light detecting system 22. The micro lens array in FIG. 5 may be replaced by a corner cube array. The CCD camera can read a plurality of emission signals at one time, and there is no need for scanning the substrate.

The apparatus and the method according to embodiments of the invention are particularly useful in determining DNA hybridization but may be useful in detecting interactions in any chemical assay. Other applications of embodiments of the method include analysis of single nucleotide polymorphism (SNP), measurement of the concentration of an ion in a cell, identification of a protein, analysis of a function of a protein, and analysis of the process or the state of metabolism, absorption, and excretion of a material dosed in an experimental mouse. Also, embodiments of the method can be applied to medical check for health care or individual certification for security system.

Although various exemplary embodiments have been shown and described, the invention is not limited to the embodiments shown. The dimensions, materials, configurations, the relative arrangements of components described in the embodiments are intended to be typical or illustrative, rather than limiting. Therefore, the scope of the invention is intended to be limited solely by the scope of the claims that follow.

What is claimed is:

1. A component for analyzing molecules, comprising:
   a transparent substrate having a plurality of pixel locations on a first surface thereof, each location including at least one target molecule,
   a reflecting plate arranged to face an opposite side of the first surface of said substrate, and
   a micro lens array interposed between said substrate and said reflecting plate, which comprises a first lens array next to said substrate, a second lens array next to said reflecting plate, and a medium layer interposed between said first and second lens arrays, wherein each lens of said second lens array has its focus on each opposing lens of said first lens array, and said first lens array and said second lens array focus into an image of each of said target molecules on said reflecting plate.

2. A component according to claim 1, wherein said at least one target molecule comprises at least one biological material selected from the group consisting of cells; proteins; genes; EST's, or other DNA sequences; ligand; receptor; peptide; and nucleic acid.

3. A component according to claim 1, wherein each reflective index of said first lens array, said medium layer, and said second lens array is different.

4. A component according to claim 1, wherein said medium layer is made of resin.

5. A component according to claim 1, wherein said medium layer is made of gas.

6. A component according to claim 1, wherein said reflecting plate at least one of permeates and absorbs light that has predetermined wavelength.

7. A light detecting apparatus, comprising
   a component according to claim 1,
   an excitation beam generator arranged to apply an excitation beam to said at least one target molecule on said substrate, and
   a light detector arranged to detect an emission signal emitted from at least one of said at least one target molecule.

8. A component for analyzing molecules, comprising
   a transparent substrate having a plurality of pixel locations on a first surface thereof, each location of which includes at least one target molecule, and
   a corner cube array arranged to face an opposite side of the first surface of said substrate which is designed to reflect an incoming ray of light exactly in the same direction as which it enters into said corner cube array.

9. The component according to claim 8, wherein said corner cube array is designed to at least one of permeate and absorb light having a predetermined wavelength.

10. A light detecting apparatus, comprising
    a component according to claim 8,
    an excitation beam generator arranged to apply an excitation beam to said at least one target molecule on said substrate, and
    a light detector arranged to detect an emission signal emitted from at least one of said at least one target molecule.

* * * * *